United States Patent
Silvestrini et al.

(10) Patent No.: US 6,269,554 B1
(45) Date of Patent: Aug. 7, 2001

(54) COMBINED PRONATION AND SUPINATION CONTROL PLANTAR INSERT FOR SHOES

(76) Inventors: Bruno Silvestrini, Via Michelangelo Schipa, 15, 00179 Rome; Camillo Buratto, Via Leonardo Da Vinci, 9; Alberto Buratto, Corso Mazzini, 50, both of 31044 Montebelluna, all of (IT)

( * ) Notice: Subject to any disclaimer, the term of this patent is extended or adjusted under 35 U.S.C. 154(b) by 0 days.

(21) Appl. No.: 09/347,302

(22) Filed: Jul. 6, 1999

(30) Foreign Application Priority Data

Jul. 7, 1998 (IT) ............................... TV98A0101

(51) Int. Cl.[7] .................................................. A61F 5/14
(52) U.S. Cl. ................................. 36/144; 36/140
(58) Field of Search ........................ 36/97, 140, 142, 36/143, 144, 150, 155, 156, 157, 81, 117.5

(56) References Cited

U.S. PATENT DOCUMENTS

| | | | |
|---|---|---|---|
| 1,662,814 | * | 3/1928 | Alfred . |
| 2,183,197 | * | 12/1939 | Kohlruss . |
| 2,205,753 | * | 6/1940 | Svrlinga, Jr. . |
| 2,212,414 | * | 8/1940 | Burger . |
| 4,253,252 | * | 3/1981 | Eisenberg . |
| 4,546,558 | * | 10/1985 | Perini . |
| 4,909,768 | * | 3/1990 | O'Brien . |
| 5,090,139 | * | 2/1992 | Germann . |
| 5,404,658 | * | 4/1995 | Rosen . |

FOREIGN PATENT DOCUMENTS

| | | |
|---|---|---|
| 2638617 | 5/1990 | (FR) . |
| 2652260 | 3/1991 | (FR) . |
| 780769 | 8/1957 | (GB) . |

* cited by examiner

Primary Examiner—Ted Kavanaugh
(74) Attorney, Agent, or Firm—Guido Modiano; Albert Josif; Daniel J. O'Byrne

(57) ABSTRACT

A combined pronation and supination control plantar insert for shoes comprising posture control elements adapted to correct and/or modify the posture of the entire tendon, bone and muscle structure of the body, both laterally and medially and both for talipes equinus and for talipes calcaneus. The plantar insert allows to correct the main postural defects involving mastication, cervical structures, the spinal column, hips, ankles and feet.

11 Claims, 3 Drawing Sheets

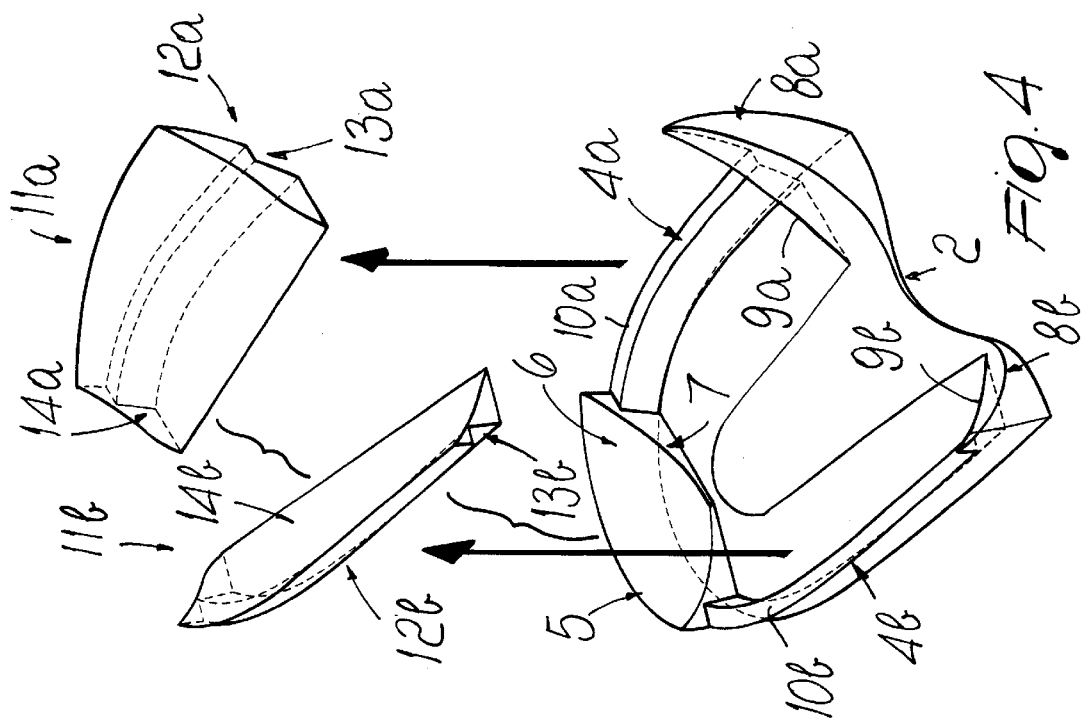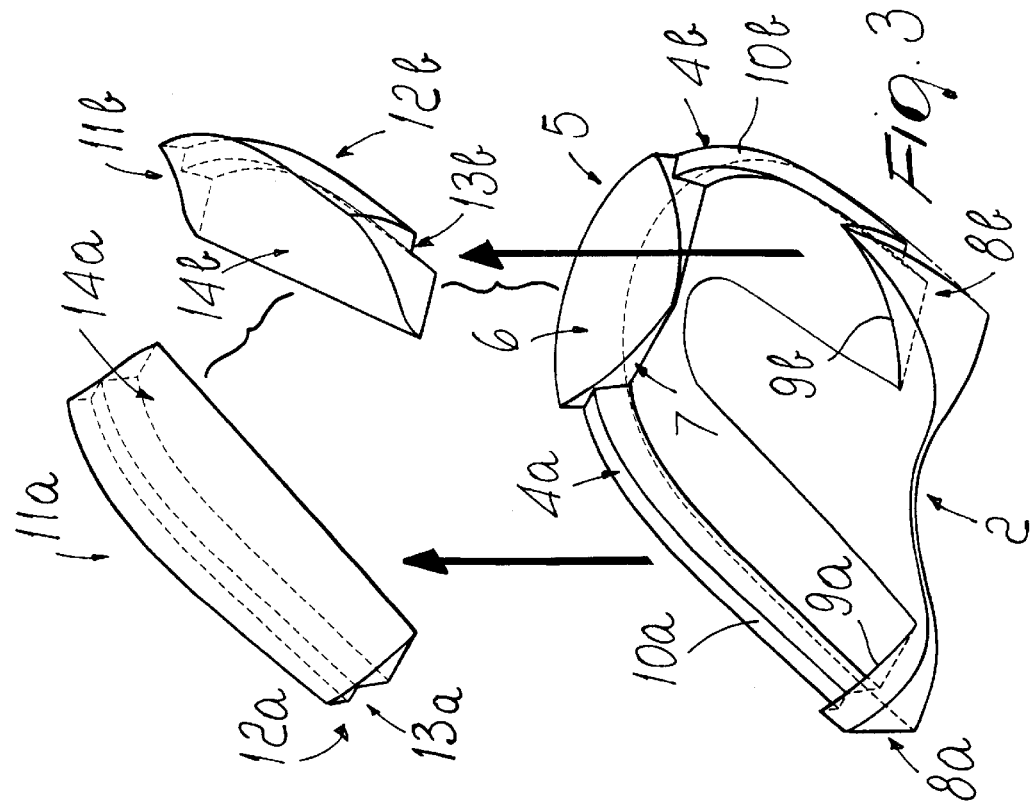

COMBINED PRONATION AND SUPINATION CONTROL PLANTAR INSERT FOR SHOES

BACKGROUND OF THE INVENTION

The present invention relates to a combined pronation and supination control plantar insert for shoes.

From a functional point of view, the foot behaves like a propeller whose blades are constituted by the hindfoot and the forefoot.

The rolling action of a step can be seen as consisting of three phases: a first contact phase, a second resting phase and a third propulsion phase.

During the first contact phase, the foot tends to pronate and therefore arrange itself inward; during the second resting phase, the foot stiffens and tends to supinate, so that the weight tends to shift toward the outer part of the foot; during the third propulsion phase, the foot is in a central position with a slight pronation in order to give impetus to the step.

All these movements of the foot can be considered equivalent to the motion of a propeller.

Therefore, depending on the motion of the blades, the foot relaxes and flattens or stiffens and therefore becomes hollow.

These two relaxation and stiffening phases are the two movements that occur alternatively in the foot during upright posture, running and jumping, and are known as pronation and supination respectively.

The deformities commonly known as flatfoot and hollow foot are due to predominant or persistent pronation (flatfoot) or supination (hollow foot).

Ready-made plantar inserts are commercially available in order to control the movement of the foot but they are usually scarcely useful.

Their use is often discretionary and can cause damage if said plantar inserts are incautiously worn by careless users.

Customizable plantar inserts manufactured by specialized technicians are an altogether different matter.

In this case, the final product is customized and perfectly matches the foot of the patient.

However, this requires the aid of labor-intensive techniques (plaster cast of the foot and creation of a complementary shape, assembly of different materials, refinement of the complementary shape according to the defect to be corrected, etcetera) and accordingly entails long production times.

Costs are high and it is impossible to modify the configuration of said plantar inserts if changes in the foot and/or in the structure of the bones, joints and muscles occur.

All these are only some of the main problems of this kind of plantar inserts.

It should also be noted that the bad posture of the feet does not affect only the bone, joint and muscle structures of said foot, causing various localized disorders; it also affects the entire supra- and subsegmental posture; accordingly, alterations can occur which affect not only the foot and the joints closest to it (talocrural joint, coxofemoral joint, knee joint) but also more distal articulations (interchondral joints, costovertebral joints, etcetera).

Many of the alterations affecting the cervical column and related symptoms, reaching as far as the temporomandibular joint with consequences for mastication, can in all likelihood originate from the incorrect static and dynamic posture of the foot.

SUMMARY OF THE INVENTION

The aim of the present invention is to solve the above-described problem, eliminating the drawbacks of the cited prior art and thus providing a plantar insert which allows to correct the main defects or problems of the foot.

Within the scope of the above aim, an important object is to provide a plantar insert which not only allows to compensate and correct flat feet and hollow feet by controlling and/or correcting pronation and supination but also allows this correction in a progressive and gradual form, so as to make it more acceptable to the patient and adapted for the current configuration of his bone, joint and muscle structures, said gradualness of the correction being more important during the developmental period.

Another important object is to provide a plantar insert which can be manufactured in a short time and can be equally applied to the various cases of correction of the cited defects, thus allowing accurate customization for any possible specific case.

Another object is to provide a plantar insert which has low manufacturing costs and can be customized in a short time to the specific defect to be corrected for a single and specific user.

This aim, these objects and others which will become apparent hereinafter are achieved by a combined pronation and supination control plantar insert for shoes, characterized in that it comprises posture control means adapted to correct and/or modify the posture of the entire tendon, bone and muscle structure of the body.

Advantageously, said means are constituted by one or more elements which can move on one or more adjustable planes arranged in a chosen point of the plantar insert.

BRIEF DESCRIPTION OF THE DRAWINGS

Further characteristics and advantages of the invention will become apparent from the following detailed description of a particular but not exclusive embodiment, illustrated only by way of non-limitative example in the accompany drawings, wherein:

FIGS. 3 and 4 are two side perspective views of the heel region without the sliding block;

DESCRIPTION OF THE PREFERRED EMBODIMENTS

Figure 1:
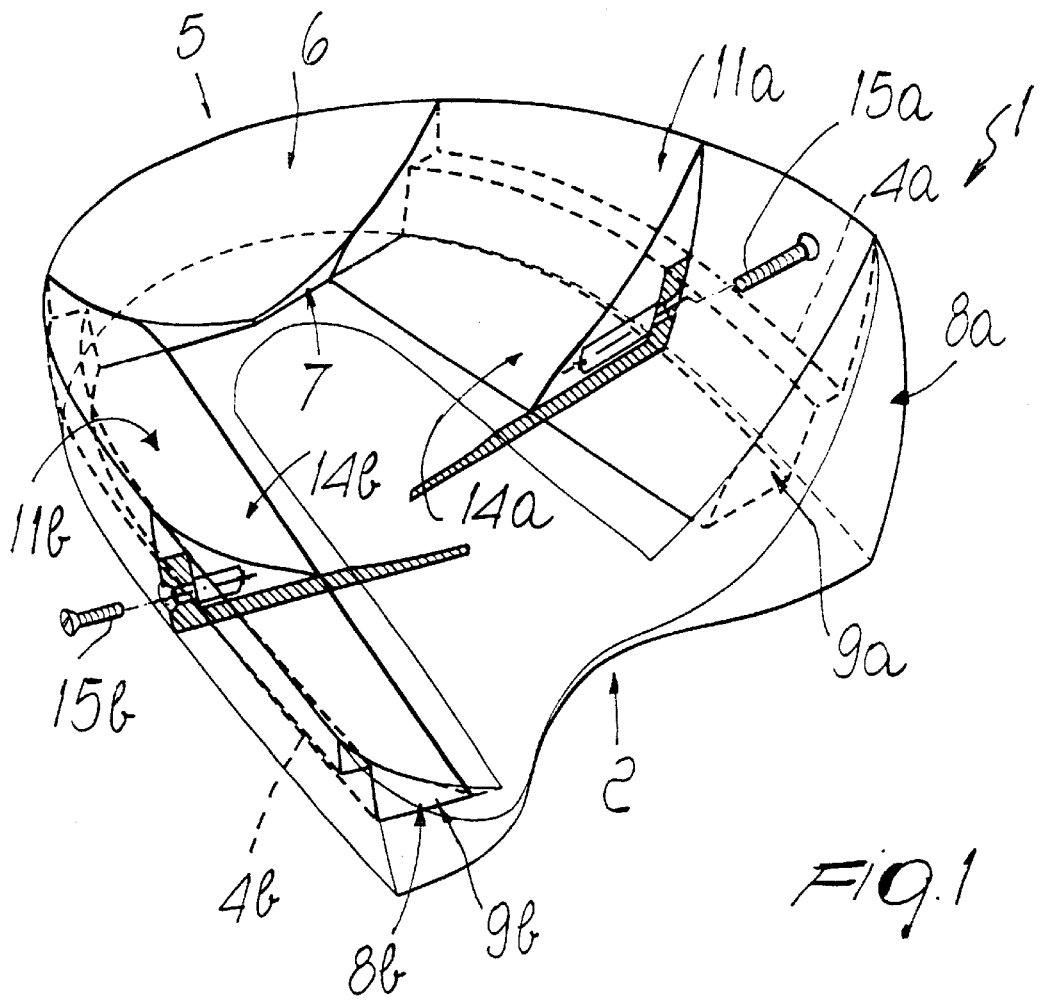
FIG. 1 is a first partially sectional lateral perspective view of the heel region of the plantar insert, on which the posture control means are associated.
Figure 2:
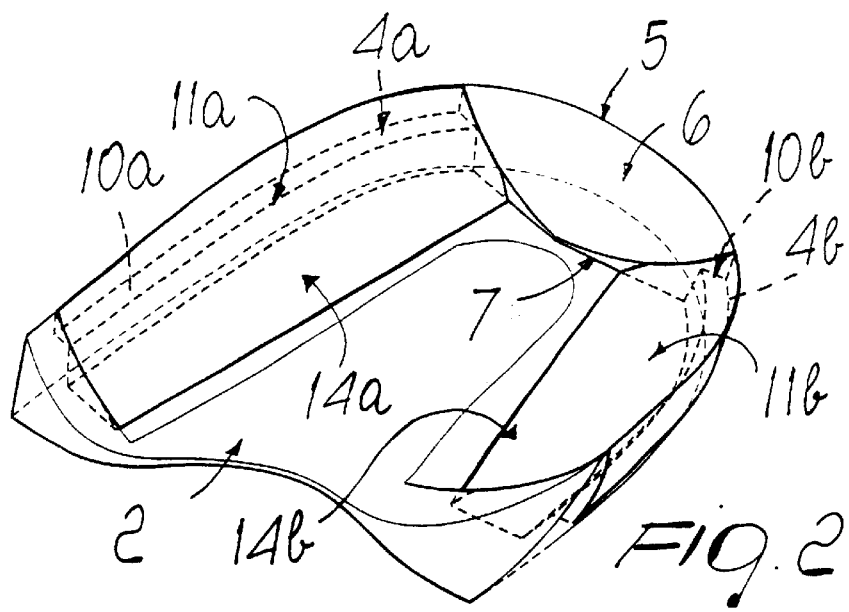
FIG. 2 is a second side perspective view of the heel region.
Figure 5:
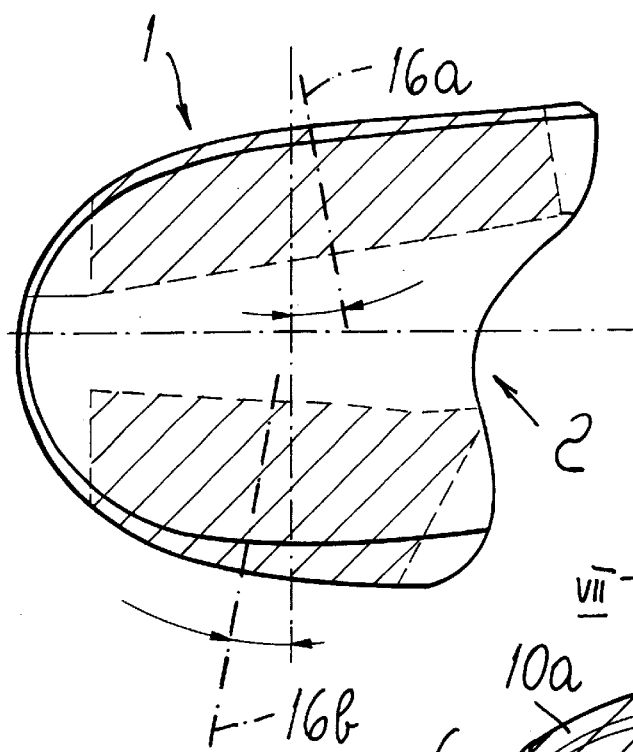
FIG. 5 is a bottom view of the heel region of the plantar insert.
Figure 6:
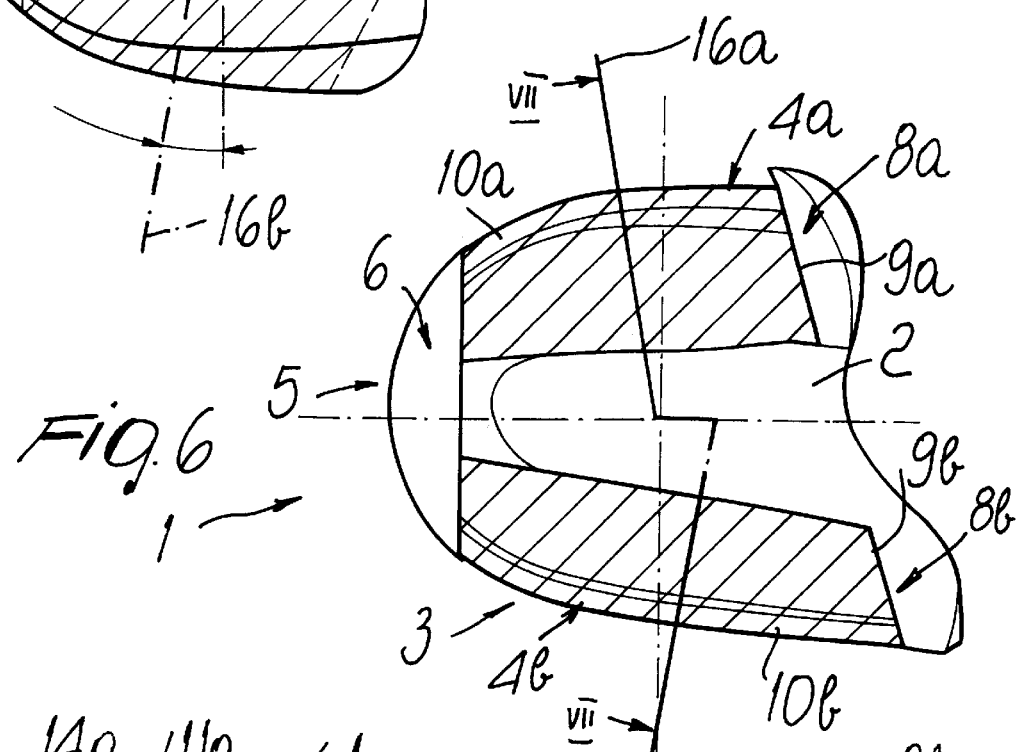
FIG. 6 is a top view of the heel region of the plantar insert.
Figure 7:
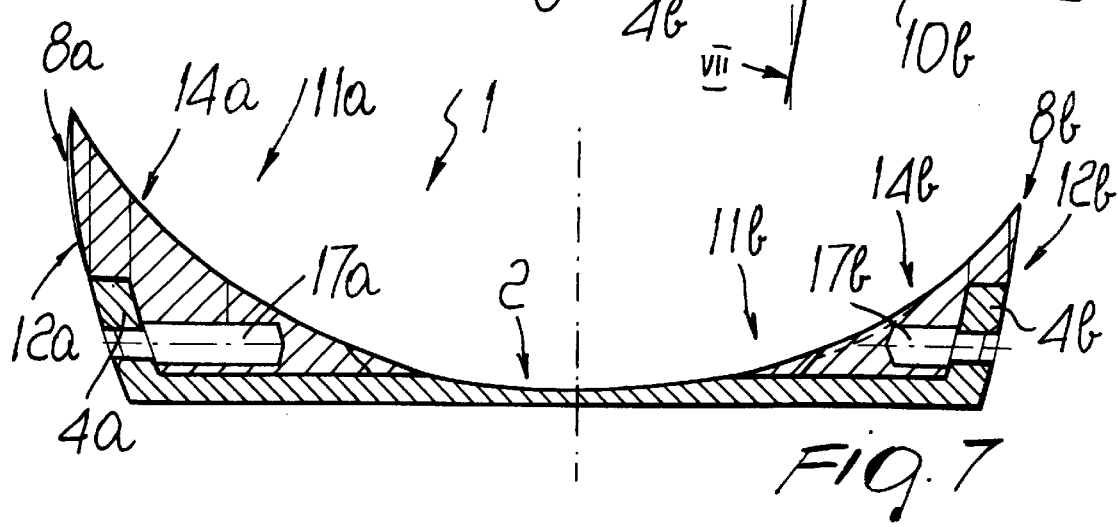
FIG. 7 is a sectional view, taken along the plane VII—VII of FIG. 6.

With reference to the above figures, an example is given of a particular application of the posture control means for correcting and/or modifying the posture of the entire tendon, bone and muscle structure of the body by placing it in the heel region 1; as an alternative, said posture control means can be placed not only in the hindfoot but also in the midfoot or also in the forefoot or can be placed exclusively in the hindfoot or in the midfoot or in the forefoot.

In the illustrated solution, therefore, the plantar insert has, in the heel region 1, posture control means which are adapted to correct and/or modify the posture of all of the bone and tendon structure of the body; this placement may be preferred for the problem of pronation and supination and therefore may be aimed at hollow or flat feet.

Said posture control means provide, at the heel region 1, a rigid base 2 having a perimetric ridge 3 which forms two first lateral arc-like wings 4a and 4b blended, in a rear region, to a second wing 5 which has a concave upper surface 6 which is blended with the base 2 by way of a first wall 7 which is perpendicular thereto and lies on an axis which is approximately transverse with respect to the axis of the heel region 1 or is conveniently inclined with respect to it.

The first lateral wings 4a and 4b are instead blended, in a front region, with a pair of third wings 8a and 8b which blend with the base 2, forming second walls 9a and 9b which are inclined with respect to an axis which runs transversely to the heel region 1.

Both the first wall 7 and the second walls 9a and 9b have tips which protrude beyond the upper perimetric edge 10a and 10b of the first lateral wings 4a and 4b so as to form guiding seats for elements which can move with respect to the base 2 and can be adjusted; said elements are constituted by two sliding blocks 11a and 11b.

Each one of said blocks has an external lateral surface 12a and 12b which has a step-like discontinuity 13a and 13b which is shaped complementarily to the first lateral wings 4a and 4b, and the dimensions of the blocks are such as to allow them to slide between the first wall 7 and the second walls 9a and 9b of the second wing 5 and of the third wings 8a and 8b respectively.

Each block also has an internal lateral surface 14a and 14b which is shaped conveniently and therefore arc-like and is blended with the concave upper surface 6 of the second wing 5 so as to constitute supporting regions for the overlying part of the foot.

Adjustment of the position of the movable elements, and therefore the possibility to adjust them in terms of their position with respect to the base 2, is provided by means of at least one pair of screws 15a and 15b which are freely rotatably associable at suitable seats formed transversely with respect to the first lateral wings 4a and 4b along axes, designated by the reference numerals 16a and 16b, which do not coincide with the axis that runs transversely to the heel region 1.

The blocks slide with respect to the base 2 because the ends of the screws 15a and 15b are rotatably associable at complementarily threaded seats 17a and 17b formed at the facing external lateral surfaces 12a and 12b of the blocks 11a and 11b.

The simple adjustment of the position of the blocks with respect to the base 2 therefore allows to customize, according to the specific defect to be corrected and therefore to the specific anatomical shape of the user, the configuration of the plantar insert, by varying the position of the blocks at the level of the hindfoot in the medial and lateral region, so as to control, for example, pronation and supination.

These adjustments are performed rapidly and easily.

It has thus been found that the invention has achieved the intended aim and objects, a combined pronation and supination control plantar insert having been obtained which allows to correct the main defects or problems affecting the position of the foot by varying the position of the movable elements with respect to the base of the plantar insert in the chosen region of the foot.

The invention is of course susceptible of numerous modifications and variations, all of which are within the scope of the same inventive concept.

Thus, for example, the posture control means adapted to correct and/or modify the posture of the entire tendon, bone and muscle structure of the body may be constituted not only by blocks but also by wedges, sliders or other equivalent means, and their position may be adjusted by virtue of means which are equivalent to the screws, allowing to use optional flexible interposed elements, such as springs or blocks made of plastics or other suitable material.

To spatially orientate the posture control means, a ball joint being positionable and lockable at various manners and locations, may be used.

Moreover, as an alternative, the wedge system may instead use a different system which allows the foot resting surface to tilt, and therefore be adjusted, in the various spatial planes by way of a spherical articulation (solid or hollow spherical segment) which inherently has many degrees of freedom.

The system can then be locked in a given position, compensating and/or correcting the configuration of the sole of the foot.

Likewise, said system can be an independent object which can be fitted in conventional shoes or in specifically provided shoes or can be an integral part of shoes designed specifically for this purpose and marketed as such.

The materials and the dimensions that constitute the individual components of the plantar insert and said elements may of course be the most pertinent according to specific requirements.

The disclosures in Italian Patent Application No. TV98A000101 from which this application claims priority are incorporated herein by reference.

What is claimed is:

1. A combined pronation and supination control shoe plantar insert for controlling posture of a user body, comprising a base element and posture control means for correcting and modifying the posture of the entire tendon, bone and muscle structure of the user body, said posture control means comprising at least one element which is movable transversely with respect to a longitudinal axis of said base, in a plane which is parallel to a plane in which said base is defined, said at least one element being adapted to vary the height of the user at a hindfoot, in a medial and lateral region of the foot, the plantar insert further including a heel region extending along a longitudinal axis thereof, at which said posture control means are located, said heel region comprising: a rigid base which has a perimetric ridge forming a pair of first arc-like lateral wings; a second wing; a first wall being perpendicular to said base and lying on an axis which is substantially transverse to the axis of said heel region; said first lateral wings joining in a rear region of the base with said second wing which has a concave upper surface connected to said base by way of said first wall.

2. The plantar insert of claim 1, wherein said posture control means are located at any of a hindfoot, midfoot and forefoot region of the foot of a user.

3. The plantar insert of claim 1, including a heel region extending along a longitudinal axis thereof, at which said posture control means are located, said heel region comprising: a rigid base which has a perimetric ridge forming a pair of first arc-like lateral wings; a second wing; a first wall being perpendicular to said base and lying on an axis which is substantially transverse to the axis of said heel region; said first lateral wings joining in a rear region of the base with said second wing which has a concave upper surface connected to said base by way of said first wall.

4. The plantar insert of claim 3, wherein said first wall and said second walls have tips which protrude beyond an upper perimetric edge of said first lateral wings, so as to form guiding seats for said at least one element which is adjustably movable with respect to said base.

5. The plantar insert of claim 4, wherein said at least one element comprises an outer lateral surface which has a step-like discontinuity, said discontinuity being shaped complementarily to said fist lateral wings, dimensions of said at least one element being such as to allow the element to slide laterally and medially as well as vertically between said first wall and said second walls, respectively, of said second win and of said third wings.

6. The plantar insert of claim 5, wherein each one of said at least one element has an internal lateral she which is shaped arc-like and joins with said concave upper surface of said second wing so as to constitute supporting regions for an overlying part of the user foot.

7. The plantar insert of claim 6, comprising at least one pair of set screws, and complementarily threaded seats formed transversely to said first lateral wings along an axis being offset with respect to an axis that runs transversely to said heel region; position adjustment of said at least one movable element with respect to said base being provided by way of said at least one pair of set screws which ate freely rotatably associable at said suitable seats.

8. The plantar insert of claim 7, comprising threaded seats formed at facing outer lateral surfaces of said at least one element, said screws being partially rotatably associated at said complementarily threaded seats so as to allow sliding of said at least one element with respect to said base.

9. The plantar insert of claim 8, wherein said first wall and said second walls are inclined with respect to the axis which runs transversely to said heel region.

10. The plantar insert of claim 9, wherein said screws are positioned so as to be in any of a perpendicular and inclined position, with respect to said outer lateral surfaces of said at least one element.

11. The plantar insert of claim 1, comprising two third wings, said first lateral wings being connected, in a front region of the base, to said two third wings which are further connected to said base, so as to form second walls, said second walls being arranged at an angle with respect to an axis which lies transversely to said heel region.

* * * * *